United States Patent
Grzesek

(10) Patent No.: US 6,614,719 B1
(45) Date of Patent: Sep. 2, 2003

(54) ULTRASONIC DOPPLER EFFECT SPEED MEASUREMENT

(75) Inventor: Robert Grzesek, Redondo Beach, CA (US)

(73) Assignee: Mattel, Inc., El Segundo ( * ) Notice: Subject to any disclaimer, the term of this patent is extended or adjusted under 35 U.S.C. 154(b) by 0 days.

(21) Appl. No.: 10/131,116

(22) Filed: Apr. 23, 2002

(51) Int. Cl.[7] ............................................... G01S 15/58
(52) U.S. Cl. ........................................... 367/90; 367/89
(58) Field of Search ............................... 367/89, 90, 94

(56) References Cited

U.S. PATENT DOCUMENTS

| | | | | |
|---|---|---|---|---|
| 3,725,854 A | * | 4/1973 | Otsuka ......................... | 367/94 |
| 4,142,187 A | * | 2/1979 | Nakayama ................... | 340/554 |
| 4,628,317 A | * | 12/1986 | Nishikawa et al. ......... | 340/903 |
| 5,216,639 A | * | 6/1993 | Ohtsuki et al. ............... | 367/90 |
| 6,272,071 B1 | * | 8/2001 | Takai et al. .................... | 367/90 |

* cited by examiner

Primary Examiner—Ian J. Lobo
(74) Attorney, Agent, or Firm—Roy A. Ekstrand

(57) ABSTRACT

An ultrasound transducer is coupled to a transmitter having a source of ultrasound signal. A receiving ultrasound transducer is coupled to a preamplifier and mixer. The mixer is further coupled to a demodulator and filter which in turn is coupled to an amplifier and a comparator. The comparator output is coupled to a controller which performs edge detection of the comparator output signal. The transmitter produces ultrasound energy which is reflected from an object to the receiving transducer. The shift in frequency between the transmitted ultrasound energy and the reflected ultrasound energy is used to determine the speed of the object by employing doppler effect. Frequency detection is enhanced by mixing the transmitted and reflected ultrasound signals to provide a beat frequency signal.

1 Claim, 2 Drawing Sheets

US 6,614,719 B1

ULTRASONIC DOPPLER EFFECT SPEED MEASUREMENT

FIELD OF THE INVENTION

This invention relates generally to apparatus for measuring the speed of an object and particularly to low cost speed measuring apparatus suitable for applications such as toys or amusement devices.

BACKGROUND OF THE INVENTION

Within the toy or amusement device industry, a need often arises to provide measurement of a moving object. A typical environment in which a requirement for measuring object speed arises is found in toy vehicle play sets. Historically, apparatus such as plural spaced apart switches or inferred or ultrasonic detectors have been utilized for this purpose. The basic apparatus operates by measuring the time interval between the moving toy vehicles encounter with the first and second sensors or switches.

While such apparatus has enjoyed commercial success in a number of applications, there remains nonetheless a continuing need in the art for evermore improved cost effective and sophisticated speed measuring apparatus suitable for use in toys or amusement devices.

SUMMARY OF THE INVENTION

Accordingly, it is a general object of the present invention to provide an improved speed measurement apparatus. It is a more particular object of the present invention to provide an improved speed measurement apparatus which is suitable in cost and complexity for use in a toy or amusement device environment.

In accordance with the present invention there is provided for use in measuring the speed of a moving object, speed measurement apparatus comprising: an ultrasonic transmitter having a transmitting transducer and output signal source for producing ultrasonic energy; an ultrasonic receiver having a receiving transducer for receiving ultrasonic energy reflected from an object to produce a reflected signal; a mixer producing a beat frequency signal between the reflected signal and the output signal; a controller for determining the frequency of the beat frequency signal; and display means for displaying a speed value derived from the frequency of the beat frequency signal.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

DESCRIPTION OF THE PREFERRED EMBODIMENT

Figure 1:
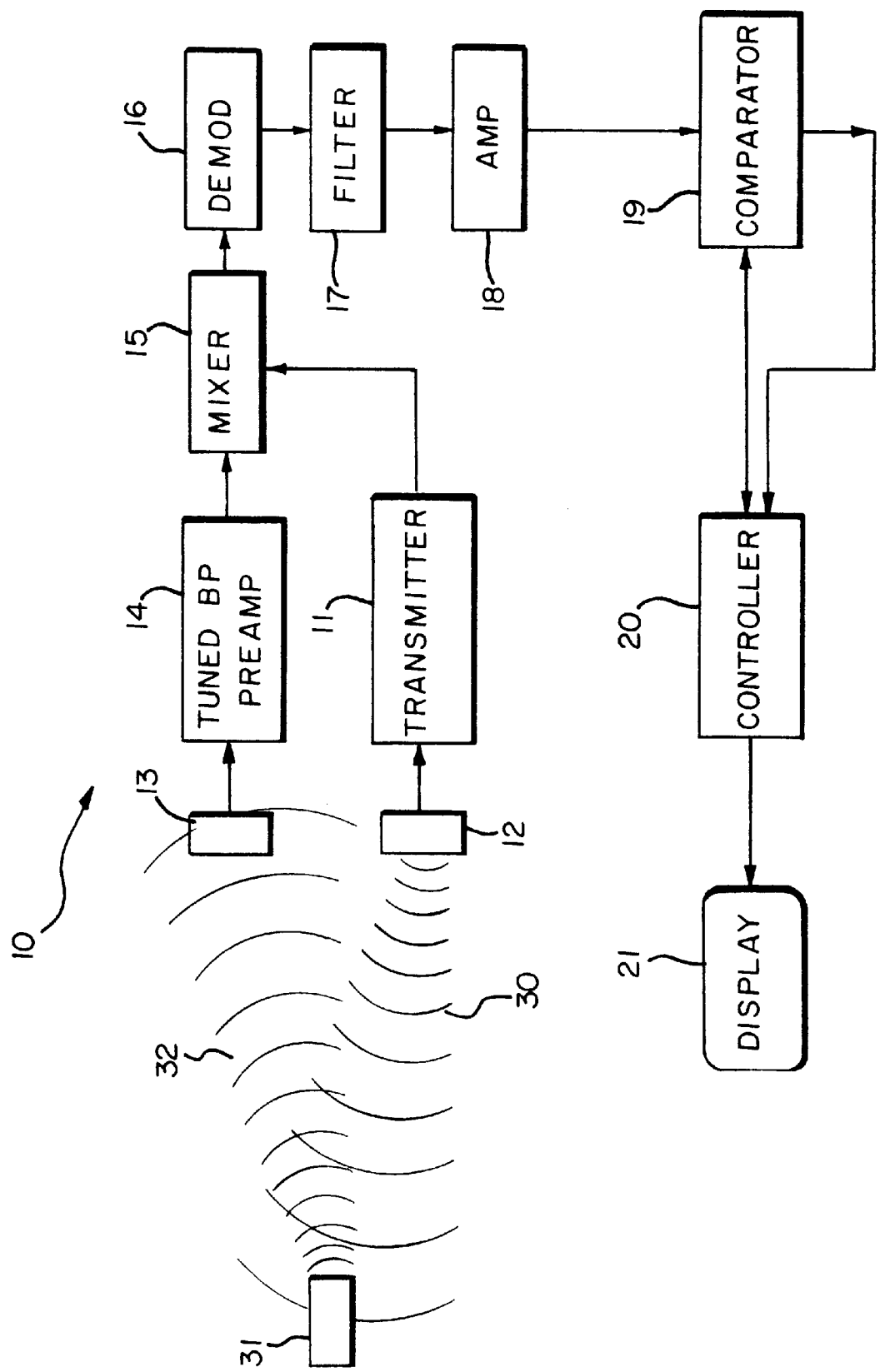
FIG. 1 sets forth a block diagram of a speed measurement apparatus constructed in accordance with the present invention.

FIG. 1 sets forth a block diagram of a speed measurement apparatus constructed in accordance with the present invention and generally referenced by numeral 10. Speed measurement apparatus 10 includes an ultrasonic transmitter 11 coupled to a piezoelectric electric transducer 12. Sound measurement apparatus 10 further includes a receiving transducer 13 coupled to a tuned bandpass preamplifier 14 which in turn is coupled to a mixer 15. Transmitter 11 is also coupled to mixer 15. The output of mixer 15 is coupled to a demodulator 16 which in turn is coupled to a filter 17 and an amplifier 18. A comparator 19 is coupled to amplifier 18 and to a controller 20. Controller 20 is further coupled to comparator 19. A display 21 is operatively coupled to and controlled by controller 20.

In operation, transmitter 11 produces an ultrasonic frequency signal such as forty kilohertz which energized piezoelectric transducer 12 producing ultrasound energy waves 30 which permeate outwardly from transducer 12. At some point, ultrasound energy waves 30 impact a moving object 31 and are reflected therefrom forming a reflected ultrasound energy wave stream 32. Reflected waves 32 impact receiving piezoelectric transducer 13 producing corresponding electric signals which are coupled to preamplifier 14. In accordance with the bandpass tuning of preamplifier 14, the received energy at transducer 13 which is at or near the forty kilohertz transmitted frequency from transducer 12 is amplified within preamplifier 14 to a substantially greater extent than other frequencies.

A portion of the forty kilohertz signal produced by transmitter 11 is coupled to mixer 15. Mixer 15 produces an output signal which includes a signal component having a frequency equal to the difference between the sample signal provided by transmitter 11 and the amplified signal from preamplifier 14. The extent to which the output of preamplifier 14 and the sample from transmitter 11 differ in frequency corresponds to the speed to which object 31 is moving due to the well known doppler effect. In essence, the doppler effect causes reflected waves from a moving object to be altered in frequency either higher or lower depending on movement direction. Accordingly, reflected waves 32 differ in frequency from transmitted waves 30 in accordance with the speed at which object 31 is moving.

The difference frequency often referred to as "beat frequency" produced at mixer 15 is applied to demodulator 16 which performs an envelope detection of the mixer output signal. Filter 17 couples the envelope signal to an amplifier 18 while reducing signal components due to interference such as noise or the like. The amplified signal output from amplifier 18 is applied to one input of a comparator 19.

A controller 20 having a calibrating voltage source therein applies the calibration voltage to the remaining input of comparator 19. The output of comparator 19 is applied to controller 20 and comprises a zero crossing or sliced portion of the output signal of amplifier 18. The important component within the output signal of comparator 19 is found in the leading and trailing edges of the greatly amplified beat frequency signal. Controller 20 includes an edge detector and timing circuit which determines the frequency of signal output from comparator 19 by counting the leading and trailing edges within the signal which occur during a preset timing interval. In this manner, comparator 20 performs frequency detection of the comparator output signal. In a typical application of the present invention speed measurement apparatus used in a toy or amusement device environment, it is anticipated that the speed likely for object 31 will be such that beat frequency signals varying between one hundred hertz and three kilohertz will be encountered. Accordingly, the timing interval for controller 20 selected in counting edges is sufficient to perform accurately upon such frequency signals. Controller 20 further converts the frequency detection of the beat frequency signal to a numeric representation which is then displayed on display 21. In the anticipated fabrication of the present invention, display 21 comprises a conventional LCD multiple segment display.

It will be recognized that the present invention speed measurement apparatus utilizes a technology similar to doppler radar in more sophisticated systems. However, the present invention system provides a substantially lower cost, substantially more practical and substantially safer apparatus suitable for use in a toy or amusement device environment.

Figure 2:
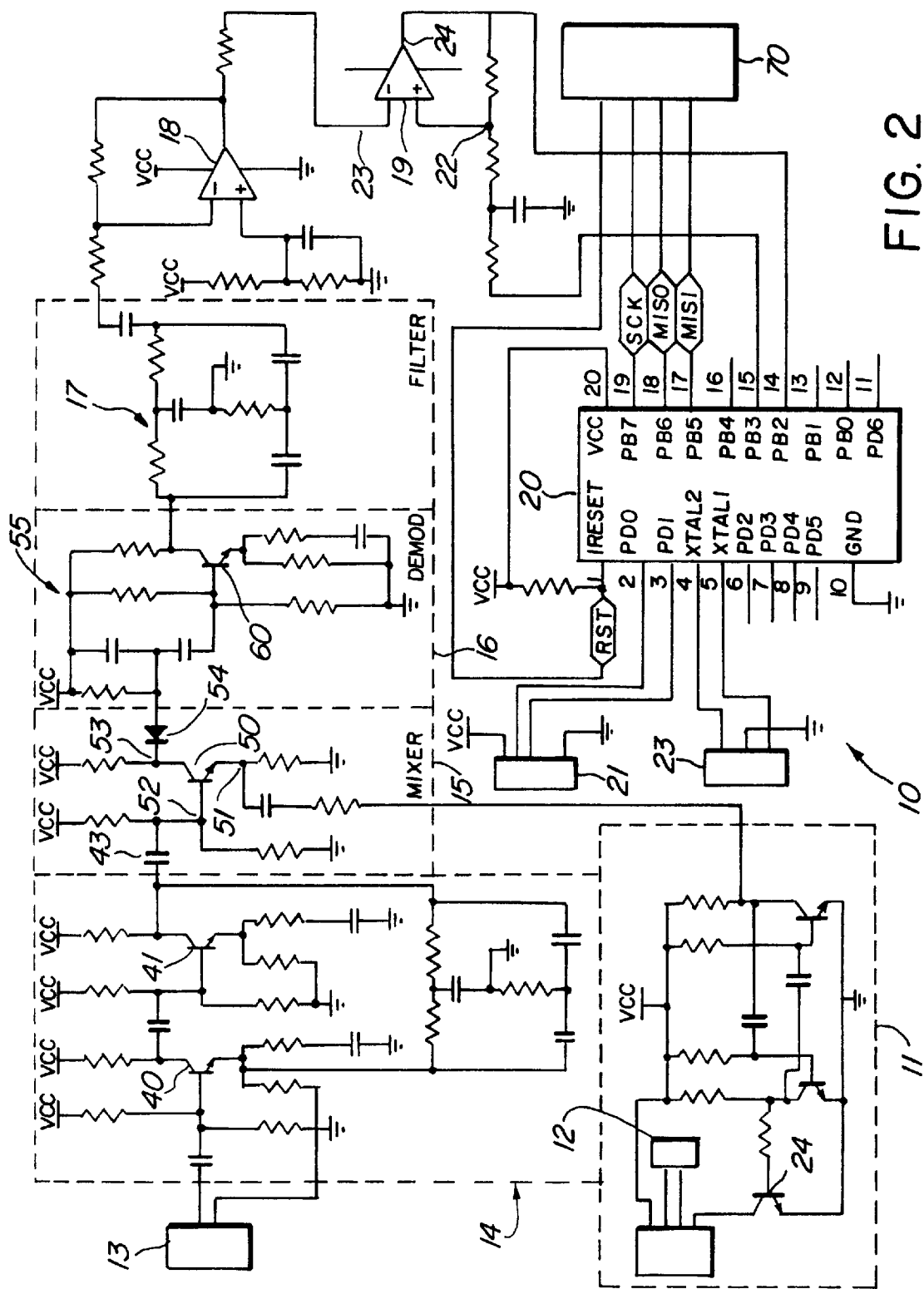
FIG. 2 sets forth a schematic diagram of the present invention speed measurement apparatus.

FIG. 2 sets forth a schematic diagram of the present invention speed measurement apparatus generally referenced by numeral 10. As described above, apparatus 10 includes a transmitter 11 having an output transducer 12. Apparatus 10 further includes a preamplifier 14 having a receiving transducer 13 coupled thereto. Apparatus 10 further includes a mixer 15 coupled to a demodulator 16 and a filter 17. Filter 17 is coupled to an amplifier 18 which in turn is coupled to a comparator 19. A controller 20 produces a dynamic reference voltage applied to comparator 19 and includes apparatus for performing edge detection and producing a numeric indication of object speed for display upon a liquid crystal display 21.

More specifically, transmitter 11 includes a free running multi vibrator of conventional fabrication which produces a periodic pulse signal having a frequency suitable for ultrasonic application such as forty kilohertz. The ultrasound signal produced by the multi vibrator is amplified by a transistor stage 24 and is coupled to transducer 12.

Preamplifier 14 includes a pair of AC coupled gain stages 40 and 41 receiving the input signal from receiving transducer 13. A notch filter 42 tuned on either side of the forty kilohertz frequency is coupled between the output of gain stage 41 and gain stage 40 to provide a negative feedback. The use of a notch filter for negative feedback between stages 40 and 41 produces an overall bandpass response at the notch frequency for the combination of gain stages 40 and 41.

A coupling capacitor 43 couples the amplified signal from preamplifier gain stage 41 to base 52 of a mixer transistor 50. Emitter 51 of transistor 50 is coupled to the multi vibrator within transmitter 11. As a result, transistor 50 performs a mixing operation upon the applied signals at base 52 and emitter 51 producing an output at collector 53 which includes the difference of beat signal between the two inputs.

The combination of a diode 54 and a lowpass filter 55 performs envelope detection upon the beat frequency signal. The envelope detected signal is applied to a gain stage 60 which in turn is coupled to notch filter 17. Notch filter 17 substantially reduces the remnant of the forty kilohertz signal within the envelope detected output of filter 55 and gain stage 60. The filtered output signal of filter 17 is amplified by amplifier 18 and applied to input 23 of a comparator 19. The remaining input 22 of comparator 19 is coupled to a dynamic control voltage produced by controller 20. In response to the applied envelope signal at input 23, amplifier 19 produces a sliced or greatly amplified output signal at output 24 of comparator 19. This output signal is applied to controller 20 which performs edge detection of the applied signal and produces a frequency indicative value which is converted to a numeric display on LCD display 21. A crystal 23 is operatively coupled to controller 20 and provides an accurate reference for the internal clock and timing apparatus of controller 20. While a number of devices may be used for controller 20, it has been found advantageous to utilize a controller manufactured by Atmel having device number AT90S2313. To further enhance the flexibility of controller 20, an access plug 70 is coupled to controller 20 and facilitates the connection of an input plug (not shown) which is utilized in downloading code to controller 20 for the purpose of updating or reprogramming or the like.

What has been shown is a novel low cost ultrasonic doppler effect speed measurement apparatus which provides relatively accurate speed measurement using safe technologies and low cost components.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. For use in measuring the speed of a moving object, speed measurement apparatus comprising:

an ultrasonic transmitter having a transmitting transducer and output signal source for producing ultrasonic energy;

an ultrasonic receiver having a receiving transducer for receiving ultrasonic energy reflected from an object to produce a reflected signal;

a mixer producing a beat frequency signal between said reflected signal and said output signal;

an envelope detector coupled to said mixer for recovering said beat frequency signal;

means for amplifying said beat frequency signal and for performing a zero-crossing sliced portion function thereon to produce a zero-crossing beat frequency signal;

an edge detector operative upon said zero-crossing beat frequency signal to produce leading and trailing edge timing signals;

a controller for determining the frequency of said zero-crossing beat frequency signal; and display means for displaying a speed value derived from said frequency of said zero-crossing beat frequency signal.

\* \* \* \* \*